(12) United States Patent
Harris et al.

(10) Patent No.: US 7,276,620 B2
(45) Date of Patent: Oct. 2, 2007

(54) PROCESS FOR PREPARING PHOSPHORODIAMIDITES

(75) Inventors: Christopher John Harris, Worcester (GB); Sheena Lesley Jackson, Birmingham (GB); David James Wilson, Stourbridge (GB)

(73) Assignee: Rhodia Consumer Specialties Limited, Watford, Hertfordshire (GB)

( * ) Notice: Subject to any disclaimer, the term of this patent is extended or adjusted under 35 U.S.C. 154(b) by 0 days.

(21) Appl. No.: 10/540,160

(22) PCT Filed: Dec. 18, 2003

(86) PCT No.: PCT/GB03/05544

§ 371 (c)(1),
(2), (4) Date: Dec. 1, 2005

(87) PCT Pub. No.: WO2004/058779

PCT Pub. Date: Jul. 15, 2004

(65) Prior Publication Data

US 2006/0128951 A1 Jun. 15, 2006

(30) Foreign Application Priority Data

Dec. 24, 2002 (GB) ................. 0230095.2

(51) Int. Cl.
*C07F 9/02* (2006.01)
(52) U.S. Cl. .................................... 558/192
(58) Field of Classification Search ............... 558/192
See application file for complete search history.

(56) References Cited

U.S. PATENT DOCUMENTS

2003/0225274 A1 12/2003 Bosch et al.
2003/0236233 A1 12/2003 Shamblee et al.

FOREIGN PATENT DOCUMENTS

| EP | 62212395 | 9/1987 |
| WO | WO 03/087130 A | 10/2003 |
| WO | WO 03/106468 A | 12/2003 |

OTHER PUBLICATIONS

Nielsen et al., Improved synthesis of 2-cyanoethyl N, N, N', N'-tetraisopropylphosphorodiamidite, (Nucleic acids Research (1987), 15 (8), 3626).*
Patent Abstracts of Japan, vol. 012 No. 075 (C-480), Mar. 9, 1988, of JP 62 212395 A, (Nippon Zeon Co. Ltd), Sep. 18, 1987.
Hamamoto S. Takaku H: "New approach to the Synthesis of Deoxyribonucleoside Phosphoramidite Derivatives", *Chemistry Letters, Chemical Society of Japan*, Tokyo, JP, vol. 8, 1986, pp. 1401-1404, XP002902766.
Pfleiderer W. et al: "Inhibition of HIV-a replication and activation of RNase L by phosphorothioate/phosphodiester 2',5'-oligoadenylate derivatives",, *Journal of Biological Chemistry, American Society of Biological Chemists*, Baltimore, Md., US, vol. 270-, No. 11, Mar. 17, 1995, pp. 5963-5978, XP002079044.
Houalla D, et al.: "Preparations ET Quelques Proprietes DE Composes Contenant LA Liaison Phosphore Trivalent-Azote", *Bulletin de La Societe Chimique de France, Societe Francaise de Chimie*, Paris, France, 1965, pp. 2368-2373, pp. 2368, 2370.
Fluka Chemika, Biochemika und Analytika Katalog 1997, Fluka Chmie AG XP002277275, p. 434.

* cited by examiner

*Primary Examiner*—J. Parsa
(74) *Attorney, Agent, or Firm*—Frishauf, Holtz, Goodman & Chick, P.C.

(57) ABSTRACT

A method of phosphorodiamidite production comprising the steps of reacting a phosphorus trihalide with a dialkyl amine in a polar solvent to form an intermediate compound. This intermediate compound is then subsequently reacted with an hydroxylalkyl compound and a dialkyl amine in the presence of a non-polar cosolvent. Following filtration to remove the solid by-product the two solvents form separate layers. This is advantageous as the upper, non-polar solvent, layer contains the high-purity phosphorodiamidite product.

13 Claims, No Drawings

PROCESS FOR PREPARING PHOSPHORODIAMIDITES

This application is a U.S. National Phase Application under 35 USC 371 of International Application PCT/GB2003/005544, filed Dec. 18, 2003.

The present invention relates to an improved method for the production of phosphorodiamidites, phosphorodiamidites produced by way of such a method and the use of such phosphorodiamidites.

Production of phosphorodiamidites has become increasingly important in the biotechnology industry. Phosphorodiamidites are used as intermediates in the manufacture of novel anti-neoplastic agents.

To be suitable for use in such industries phosphorodiamidites must be of high purity. Such phosphorodiamidites must also contain low levels of bis-(2-cyanoethyl) phosphorodiamidite (the 'diester').

This impurity is known to be a significant by product in the synthesis of 2-cyanoethyl tetraisopropylphosphorodiamidite, a commercially important intermediate in the synthesis of oligonucleotides.

As phosphorodiamidites are very air sensitive and thermally unstable, their purification is, at present, complex and expensive. Hitherto, known processes of extraction and purification of phosphorodiamidites often involve multi-stage synthetic procedures which demand the chemical isolation of intermediate materials and require extensive purification procedures prior to the isolation of high purity phosphorodiamidite products.

The present invention aims to ameliorate the aforementioned disadvantages of phosphorodiamidite production.

Accordingly, the present invention provides a method of phosphorodiamidite production which method comprises the steps of reacting a phosphorus trihalide with a dialkyl amine in a polar solvent to form an intermediate compound and subsequently reacting the intermediate compound with a hydroxyalkyl compound and a dialkyl amine, in the presence of a non-polar co-solvent.

Following filtration to remove the solid by-product, the two solvents form separate layers. This is advantageous as the upper, non-polar solvent, layer contains the high-purity phosphorodiamidite product. The lower, polar solvent, layer contains impure product contaminated with diester and other unwanted by-products. The upper layer is then subjected to vacuum-stripping to remove the solvent, leaving the desired product with greater than 96% purity and containing less than 1% of the diester impurity. The yield of the product can further be increased by optionally rewashing the polar solvent layer with a further quantity of non-polar solvent, to give non-polar solvent solution containing pure product, from which can then be isolated high-purity phosphorodiamidite.

Advantageously, impure product contaminated with diester and other impurities which would otherwise be unsuitable for commercial use can be extracted and purified by use of the solvent purification procedure. Phosphorodiamidite products are preferentially soluble in the non-polar co-solvent whereas the diester and other unwanted polar by-products are insoluble and remain in the polar solvent layer.

Preferably, the phosphorus trihalide is phosphorus trichloride. Alternatively, the phosphorus trihalide is phosphorus tribromide.

The dialkyl amine is preferably diisopropylamine. Alternatively the dialkyl amine may be dimethylamine, diethylamine, di-n-propylamine, di-n-butylamine, di-isobutylamine or di-tert-butylamine.

The polar solvent is preferably a nitrile compound, in particular, acetonitrile. Alternatively the polar solvent may be propionitrile or benzonitrile.

The hydroxyalkyl compound is preferably hydroxypropionitrile. Alternatively the hydroxyalkyl compound may be methanol, tert-butyl alcohol or other suitable hydroxyalkyl compounds which are known to be suitable for the manufacature of phosphorodiamidites.

The alkane co-solvent is preferably heptane or hexane. Other suitable $C_5$ to $C_9$ aliphatic hydrocarbons include pentane. Suitable alicyclic hydrocarbons include, for example, cyclohexane.

The ratio of polar solvent to non-polar solvent is suitably around 1:1. The method according to the invention provides a phosphorodiamidite compound according to Formula I:

$$(R_2N)_2\text{—P—O}(CH_2)_n\text{-CN} \tag{I}$$

wherein R is a $C_1$ to $C_4$ alkyl, hydroxyalkyl or oxyalkyl group; and n is a whole number of from 1 to 4.

The compound according to formula I is preferably 2-cyanoethyl tetraisopropyl phosphorodiamidite wherein R is isopropyl, and n=2.

The present invention also provides the use of a compound of formula I in the synthesis of oligonucleotides.

The present invention will now be illustrated, merely by way of example, as follows:

EXAMPLE 1

Manufacture of 2-cyanoethyl Tetraisopropyl Phosphorodiamidite using Hexane Co-solvent 27.5 g of phosphorus trichloride at ambient temperature was added to a stirred mixture of acetonitrile (200 g) and diisopropylamine (121 g) over 1 hour. 200 g of hexane is then added followed by 14 g of hydroxypropionitrile at ambient temperature over 30 minutes. The reaction mixture is then stirred for 1 hour and is then filtered to remove the solid by-product. The upper hexane layer of the filtered reaction mixture is separated and subjected to vacuum stripping to remove the hexane solvent. This leaves 20 g of 2-cyanoethyl tetraisopropylphosphorodiamidite which has a purity of 96.9% when analysed by $^{31}$P—NMR. The lower acetonitrile layer is stirred with a further 200 g of hexane for 2 hours. The upper hexane layer from this re-extraction contains product of 98% purity when assayed by $^{31}$P—NMR. Following vacuum stripping a further 11 g of high purity 2-cyanoethyl tetraisopropylphosphorodiamidite is isolated.

EXAMPLE 2

Manufacture of 2-cyanoethyl Tetraisopropylphosphorodiamidite using Heptane Co-solvent 27.5 g of phosphorus trichloride was added to a stirred mixture of 200 g of acetonitrile and 121 g of diisopropylamine at ambient temperature. 200 g of heptane was then added to this mixture followed by 14.3 g of hydroxypropionitrile at ambient temperature over 30 minutes. The reaction mixture was then stirred for an hour and was then filtered to remove the solid by-product. The upper heptane layer was then separated and subjected to vacuum stripping to remove the heptane solvent leaving 22 g of 2-cyanoethyl tetraisopropylphosphorodiamidite which had a purity of 96.7% when assayed by $^{31}$P—NMR.

EXAMPLE 3

Purification of Low Purity 2-cyanoethyl Tetraisopropylphosphorodiamidite 60 g of low purity 2-cyanoethyl tetraisopropylphosphorodiamidite (92% purity when assayed by $^{31}$P—NMR containing 1.3% diester) was added to a mixture of 200 g acetonitrile and 200 g of heptane after stirring for ten minutes the upper heptane layer was separated and the lower acetonitrile layer stirred with a further 200 g of heptane for a further 10 minutes. The second heptane fraction was then separated and the two heptane fraction subsequently combined and subjected to vacuum stripping to remove heptane solvent. 30 g of 2-cyanoethyl tetraisopropylphosphorodiamidite was obtained at a purity of 98.3% when assayed by $^{31}$P—NMR. This extracted phosphorodiamidite compound contained less than 0.1% of the diester impurity.

The invention claimed is:

1. A method of phosphorodiamidite production which method comprises the steps of reacting a phosphorus trihalide with a dialkylamine in a polar solvent to form an intermediate compound and subsequently reacting the intermediate compound with a hydroxyalkyl compound and a dialkyl amine, in the presence of a non-polar cosolvent.

2. A method as claimed in claim 1 in which the phosphorus trihalide is phosphorus trichloride.

3. A method as claimed in claim 1 in which the phosphorus trihalide is phosphorus tribromide.

4. A method as claimed in claim 1 in which the dialkyl amine is diisopropylamine.

5. A method as claimed in claim 1 in which the dialkyl amine is selected from the group consisting of dimethylamine, diethylamine, di-n-propylamine, di-n-butylamine, di-isobutylamine or ditert-butylamine.

6. A method as claimed in claim 1 in which the polar solvent is a nitrile compound.

7. A method as claimed in claim 6 in which the nitrile compound is acetonitrile.

8. A method as claimed in claim 6 in which the polar solvent is propionitrile or benzonitrile.

9. A method as claimed in claim 1 in which the hydroxyalkyl compound is hydroxypropionitrile.

10. A method as claimed in claim 1 in which the hydroxyalkyl compound is methanol or tert-butyl alcohol.

11. A method as claimed in claim 1 in which the alkane cosolvent is a $C_5$ to $C_9$ aliphatic hydrocarbon.

12. A method as claimed in claim 1 in which the alkane co-solvent is an alicyclic hydrocarbon.

13. A method as claimed in claim 1 in which the ratio of polar solvent to non-polar solvent is 1:1.

* * * * *